United States Patent [19]

Fournier et al.

[11] 4,225,611
[45] Sep. 30, 1980

[54] NOVEL N-SUBSTITUTED BENZENESULFONAMIDE, PROCESS FOR ITS PREPARATION AND MEDICAMENTS CONTAINING IT

[75] Inventors: Jean-Paul Fournier, Versailles; Patrick Choay, Paris, both of France

[73] Assignee: Choay S.A., Paris, France

[21] Appl. No.: 893,250

[22] Filed: Apr. 5, 1978

[30] Foreign Application Priority Data

Apr. 5, 1977 [FR] France .................... 77 10322

[51] Int. Cl.$^2$ ............... A61K 31/40; C07D 207/08
[52] U.S. Cl. .................. 424/274; 260/141; 260/239.6; 260/239.65; 260/543 R
[58] Field of Search ............ 260/239.6, 239.65; 424/274

[56] References Cited

U.S. PATENT DOCUMENTS 4,064,264  12/1977  Nelson ................... 424/274

FOREIGN PATENT DOCUMENTS 827446  5/1958  United Kingdom ........... 260/239.6

OTHER PUBLICATIONS

Morrison et al., Organic Chemistry, 2nd Ed., frontispage, pp. 666, 667, 706, 707, 760, 761, Allyn and Bacon, Inc. Boston, Mass.
Hendrickson et al., Organic Chemistry, Third Ed., p. 539, McGraw-Hill Book Co. (NY).
Chemical Abstracts, vol. 54, cols. 14189-14190 (1960), (abst. of Brit. Pat. No. 827,446).
Northey, The Sulfonamides and Allied Compounds, pp. 11-14 and 155-162, Reinhold Publishing Corp. NY (1948).

*Primary Examiner*—John D. Randolph
*Attorney, Agent, or Firm*—Weiser, Stapler & Spivak

[57] ABSTRACT

Amino-4 chloro-5 methoxy-2 N-(N-ethyl methyl-2 pyrrolidino) benzenesulfonamide is a novel compound corresponding to the formula

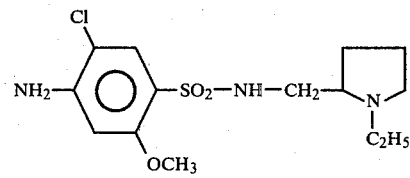

and is prepared by reacting sulfonyl chloride of the formula

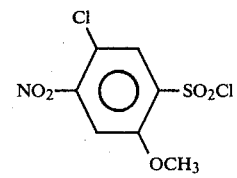

with the amine of the formula

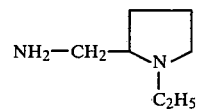

This compound and its addition salts with physiologically acceptable mineral or organic acids, is a useful medicament for the treatment of ulcerous gastro-duodenal disorders.

10 Claims, No Drawings

NOVEL N-SUBSTITUTED BENZENESULFONAMIDE, PROCESS FOR ITS PREPARATION AND MEDICAMENTS CONTAINING IT

The invention relates to a novel N-substituted benzenesulfonamide, to the process for preparing it and to medicaments containing it.

The N-substituted benzenesulfonamide of the present invention corresponds to the formula

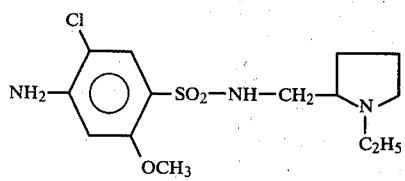

The invention also relates to the addition salts of this N-substituted benzenesulfonamide, notably with physiologically acceptable mineral or organic acids.

A method for preparing the N-substituted benzenesulfonamide according to the invention consists of preparing the benzenesulfonyl chloride of the formula

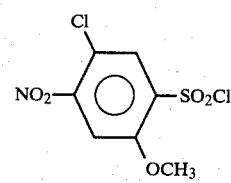

reacting this sulfonyl chloride (II) with the amine corresponding to the formula

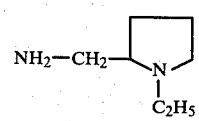

and then reducing the $NO_2$ group to $NH_2$ by catalytic hydrogenation.

The benzenesulfonyl chloride (II) can be obtained from amino-2 chloro-4 nitro-5 anisole by operating in the manner described in French Patent Application No. 76 01685, namely:

(a) starting from this arylamine, the diazonium salt is formed, notably by reacting the amine in solution in hydrochloric acid with a solution of an alkali metal nitrite, the reaction mixture being kept at a temperature below 10 C:

(b) the diazonium salt thus obtained is reacted in solution with sulfur dioxide; preferably, the operation is carried out in the presence of acetic acid and a catalyst, notably based on copper (modified Sandmeyer reaction).

The reaction diagram for the preparation of benzenesulfonyl chloride is:

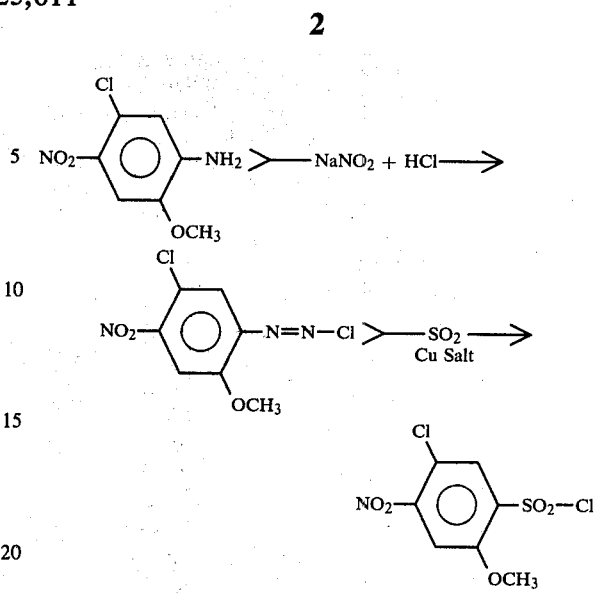

The preparation of the benzenesulfonamide is then carried out according to the following scheme:

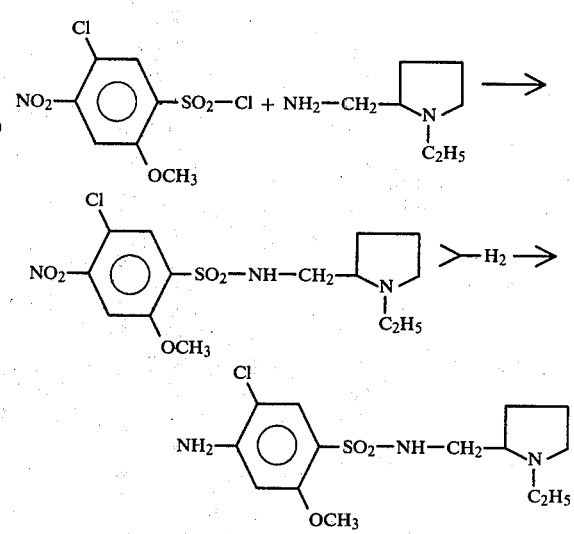

The following example illustrates in detail a method of preparing the compound according to the invention.

Preparation of chloro-5 methoxy-2 nitro-4 benzenesulfonyl chloride (a) Preparation of chloro-4 nitro-2 phenol In a triple-necked flask of 125 ml provided with a stirrer system and a thermometer 0.125 mole (16 g) of chloro-4 phenol, 25 ml of water and 35 ml of acetic acid are introduced. The mixture is taken to 40° C., and then drop by drop 14.2 ml of nitric acid (d=1.38) are added; it is left in contact 5 hours. The product is separated by filtration and crystallized in the minimum of absolute alcohol.

Yield=98% theor.

M.P.=85° C.

(b) Preparation of chloro-4 nitro-2 anisole

In a 250 ml triple-necked flask provided with a stirrer system, a thermometer and a refrigerant, 0.072 mole (12.6 g) of chloro-4 nitro-2 phenol, 40 ml of acetone and 9.72 g of potassium carbonate are introduced. The mixture is taken to 40° C., and then drop by drop 9.72 g of dimethyl sulfate added. The mixture is heated under reflux for 5 hours; the potassium sulfate is separated; the acetone solution is concentrated under reduced pressure, and the chloro-4 nitro-2 anisole precipitates. It is separated, and then crystallized in a water/acetone mixture.

Yield = 85% theor
M.P. = 85° C.

(c) Preparation of amino-2 chloro-4 anisole 0.037 mole (7 g) of chloro-4 nitro-2 anisole is dissolved in 100 ml of absolute alcohol; 3 g of RANEY nickel is added. The solution is hydrogenated at atmospheric pressure and at ambient temperature with stirring. It is separated, and then the catalyst is washed with two lots of 20 ml of boiling ethanol. The alcoholic solution is concentrated under reduced pressure: the amino-2 chloro-4 anisole crystallizes.

Yield = 80% theor.
M.P. = 84° C.

(d) Preparation of acetamido-2 chloro-4 anisole

In a 150 ml flask, 0.2 mole (31.5 g) of amino-2 chloro-4 anisole, 40 ml of absolute alcohol and 20 ml of acetic anhydride are introduced, and a pinch of zinc powder; the solution is taken to reflux for 30 minutes. The reaction liquid is poured onto crushed ice. The product obtained is separated. It is crystallized in a methanol/water (20-80) mixture.

Yield = 93% theor.
M.P. = 102° C.

This yield can be further improved by operating in a reducing medium.

(e) Preparation of acetamido-2 chloro-4 nitro-5 anisole

Into a 1000 ml triple-necked flask, 168 ml of NORDHAUSEN sulfuric acid (20% sulfur trioxide) are placed which is cooled to +5° C., and then in small portions 0.42 mole (84 g) of acetamido-2 chloro-4 anisole is added. Then drop by drop a mixture constituted by 44.4 ml of nitric acid and 37.2 ml of fuming sulfuric acid are introduced; the mixture is taken to room temperature and allowed to stand in contact with stirring for 6 hours; then it is poured over crushed ice; the product precipitates, it is separated, then washed abundantly with ice water.

Yield = 68% theor.
M.P. = 185° C.

In the course of this reaction, secondary products are formed; by washing the precipitate obtained with dilute alcohol, a product has been isolated which, after treatment with potassium hydroxide in an aqueous medium, has been identified as amino-2 chloro-4 anisole.

(f) Preparation of amino-2 chloro-4 nitro-5 anisole

Into a 500 ml flask are introduced 0.5 mole (99.5 g) of acetamido-2 chloro-4 nitro-5 anisole and 125 ml of a solution of potassium hydroxide (140 g of KOH/100 ml of water); the mixture is taken to between 100° and 110° C. for one hour and three quarters; the product is dried and washed with water.

Yield = 81% theor.
M.P. = 131° C.

(g) Preparation of chloro-5 methoxy-2 nitro-4 benzenesulfonyl chloride 0.1 mole (20.2 g) of amino-2 chloro-4 nitro-5 anisole is dissolved in 60 ml of hydrochloric acid (d = 1.18). The amine is diazotised between 0° and +5° C. by the addition of 10 g of sodium nitrate in solution in 50 ml of water.

On the other hand, to 100 ml of pure acetic acid are added 7 g of cupric chloride dissolved in a minimum amount of water; the solution is saturated in the cold with sulfur dioxide.

The freshly prepared diazonium salt is poured slowly into the acetic solution with stirring. When nitrogen ceases to be evolved, the reaction medium is diluted with ice water; the sulfochloride precipitates, and it is separated and dried.

Yield = 66% theor.
M.P. = 100° C.

Preparation of the amine (III)

The technique described by H. REITSEMA and reported in J. of American Chemical Soc. (1949), p. 2041-42 is followed.

N-ethyl chloro-3 piperidine hydrochloride, in the proportion of 36.8 g (0.2 mole) is added to 50 cm$^3$ of water supplemented with 42.8 g (0.4 mole) of benzylamine.

The mixture is taken to a temperature of 65° to 75° C. After 48 hours, the reaction medium is supplemented with 60 cm$^3$ of water, then made alkaline with a sufficient amount of potassium carbonate to bring the pH to about 10. It is extracted with ethyl ether. The organic phase recovered is dried over sodium sulfate and the solvent evaporated. The residue is distilled under high vacuum (0.01 mmHg) at 110° C. In this way by distillation 11.96 g of N-ethyl-2-benzylaminomethyl pyrrolidine are obtained.

The previously obtained product is subjects to catalytic hydrogenation in the presence of 10% of palladised carbon, in 100 cm$^3$ of absolute ethanol and at 50° C. When the theoretical amount of hydrogen necessary for complete hydrogenation has been absorbed, the reaction is stopped.

After filtration of the catalyst and washing the latter, the filtrate is distilled under reduced pressure at a temperature below 45° C. By distillation the N-ethyl-2-aminomethyl pyrrolidine is obtained with a yield of 97%.

Preparation of chloro-5 methoxy-2 nitro-4 N-(N-ethyl methyl-2 pyrrolidino) benzenesulfonamide 28.6 g of chloro-5 methoxy-2 nitro-4 benzenesulfonyl chloride and 12.8 g of N-ethyl-2-aminomethyl pyrrolidine (which corresponds to an equimolar mixture) are condensed in the following manner.

The chloro-5 methoxy-2 nitro-4 benzenesulfonyl chloride is dissolved in 150 ml of anhydrous benzene. Drop by drop with stirring N-ethyl-2-aminomethyl pyrrolidine is added; the solution is heated and then becomes cloudy; the sulfamide hydrochloride formed is deposited in the form of a yellow microcrystalline powder. It is separated, then washed twice with 20 ml of ethyl ether.

If necessary, the reaction can be triggered by slight heating.

The yield of the condensation is 90%.

Preparation of chloro-5 methoxy-2 amino-4 N-(N-ethyl methyl-2 pyrrolidino) benzenesulfonamide 0.01 mole of nitrated sulfonamide are suspended in 50 ml of absolute alcohol; 3 g of nickel prepared according to RANEY are added; the mixture is hydrogenated at atmospheric pressure and at ambient temperature with stirring. The catalyst is separated and then washed twiced with 10 ml of boiling ethanol. The alcoholic solution is concentrated; by the addition of ether, the hydrochloride crystallizes in the form of white needles. It is recrystallized in isopropanol.

The melting point of the product obtained is 180° C. The elementary analysis of the product agrees with the theory.

|  | C | H | N | Cl | S |
|---|---|---|---|---|---|
| Calculated : | 43.76 | 6.03 | 10.93 | 18.45 | 8.34 |
| Found : | 43.73 | 5.97 | 10.96 | 18.68 | 8.19 |

The novel benzenesulfonamide (I) has interesting pharmacological properties. In addition to activity on the central nervous system (anticonvulsant, anti-emetic, etc.) and antibiotic activity, the compound according to the invention is distinguished by its anti-ulcer properties and a satisfactory activity/toxicity ratio.

The compound (I) is advantageously introduced as an active principle into medicaments for the treatment of ulcerous gastro-duodenal disorders.

The compound (I) is for this purpose associated with traditional excipients and adjuvants, notably those used for the preparation of tablets, capsules, powders, drinkable ampoules, injectable solutions, etc.

The administration of the medicaments containing the compound according to the invention can be carried out by the oral route or by the intravenous route. The doses administered can vary according to the mode of administration and the phase of the treatment. By way of example, for an attack treatment, preferably from 50 to 200 mg of the product is administered intravenously, or 400 to 800 mg by the oral route and daily, these doses being distributed into two lots. For maintenance treatment, it is possible to administer 200 to 400 mg of product by the oral route and daily, divided into two lots.

The results indicated below show the anti-ulcer properties of the compound according to the invention.

Determination of the acute toxicity

The acute toxicity is expressed by the lethal dose 50, that is to say the dose resulting in the death of 50% of the animals.

This study has been carried out on groups of 10 Swiss male mice whose weight varied from 24 to 26 g, and on groups of six Wistar male rats of 120 to 125 g.

The administration was made in a single dose by the oral route in the rats and the mice, and also by the intravenous route in the case of the mice.

The results, determined according to the methods of BEHRENS AND KARBER (Arch. Exp. Path. Pharm. 1935, 177, 379–388) and MILLER and TAINTER (Proc. Soc. Exp. Biol. Med., 1944, 57, 261–264), were as follows:

| in the rat, by the oral route | LD$_{50}$ | 1500 mg/kg |
|---|---|---|
| in the mouse, by the oral route | LD$_{50}$ | 1000 mg/kg |
| in the mouse, by the intravenous route | LD$_{50}$ | 130 mg/kg |

Anti-ulcer activity

The compound according to the invention was studied for its preventive properties with respect to ulcers generated by various means. Thus the ratio in the reduction of gastric attacks caused by acetyl salicylic acid and phenylbutazone was determined, as well as the ratio in the reduction of stress ulcers and SHAY ulcers, or again vasomotor reactions to polymyxine B.

For these tests, male Wistar rats were used (from 250 to 350 g according to the test). For each test and each dose, 10 animals at least were treated.

In the case of acetyl salicylic acid (AAS) and of phenylbutazone, the test procedure was as follows:

administration by the oral route of 50 mg/kg of the compound in aqueous solution with 3% of gum arabic after 23 hours fasting;

initiation of ulcerogenesis 1 hour later, by the administration of 50 mg/kg of AAS by the oral route or of 100 mg/kg of phenylbutazone by the intraperitoneal route;

sacrifice of the animals 24 hours later and examination of the gastric mucous membrane.

The control animals only received AAS or phenylbutazone.

For the stress ulcer, the rats, 1 hour after having received 50 mg/kg of the product according to the invention by the oral route, were totally immobilized for 18 hours in a cylindrical wire cage, according to the technique of ROSSI (C.R. Soc. Biol., 1956, 150, 2124–2126) and BONFILS (C.R. Soc. Biol., 1957, 151, 1149–1150). They were then sacrificed and examined.

The SHAY ulcer was produced in the fasting rat after 48 hours. 47 hours after the beginning of the fast, by the oral route, 100 mg/kg of the product to be tested was administered, then, 1 hour later, ligature of the pylorus was effected after light anesthesia with ether. The sacrifice of the animals took place 12 to 24 hours after the ligature.

In all the preceding tests, the results were obtained by examination of the gastric mucous membrane to determine the presence either of a congested area, or of more or less serious ulcerations.

Study of the levels of reduction of attacks in the treated animals, with respect to the controls, was effected by the method of O. FOUSSARD and G. NARCISSE (Therapie, 1972, 27, 705–721) applying the formula of J. M. LWOFF (J. Pharmacol., 1971, 2, 1, 81–83).

This level of reduction in the various tests was found to be:

| acetyl salicylic acid ulcer | 40.0% |
|---|---|
| phenylbutazone ulcer | 46.9% |
| stress ulcer | 50.8% |
| SHAY ulcer, after 24 hours of ligature | 46.1% |
| SHAY ulcer, after 12 hours of ligature | 60.4% |

In the tests with polymyxine B, 100 mg/kg of the compound according to the invention was administered by the oral route before the intraperitoneal injection of 1.5 mg/kg of polymyxine B, then, two hours later after this last injection, the rats were sacrificed. The injection of polymyxine B has the effect of causing vasomotor lesions and hemorhagia of the glandular portion of the stomach. It is by measurement of the extent of these lesions that the anti-ulcerogenic action of the compound was determined (A. BELL and Coll., Biologie et gastro-enterologie, 1969, 2, 117–126–Suppt. No. 2 aux Archives francaises des maladies de l'appareil digestif, 1969, 58, 10–11, October–November). The tests carried out on a batch of 15 rats compared with a batch of 15 controls showed a distinct reduction in the these lesions, of the order of 63%, by the administration of the product according to the invention.

All these tests provided evidence that the product according to the invention certainly had anti-ulcerogenic activity. The activity/toxicity ratio being very satisfactory, this product is an active principle of great interest for the preparation of medicaments, notably in the case of gastro-duodenal ulcerous disorders.

We claim:

1. A compound 4-amino-5-chloro-2-methoxy-N(N'-ethyl 2-methylpyrrolidino) benzenesulfonamide of the following formula (I)

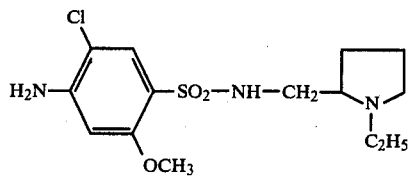

and its additional salts with physiologically acceptable mineral or organic acids.

2. A medicament comprising an effective amount of the compound of formula (I) or one or its salts according to claim 1, associated with pharmaceutically acceptable excipients or adjuvants to facilitate its administration.

3. The medicament according to claim 2, for the attack treatment of ulcerous gastro-duodenal disorders, wherein the compound of formula (I) or one of its salts is formed into intravenous unit doses between 25 and 100 mg.

4. Method of treating gastro-duodenal ulcerous disorders comprising administering to the patient a therapeutically effective amount of a compound according to claim 1.

5. Method of treating gastroduodenal ulcerous disorders comprising administering to the patient a medcament according to claim 2.

6. The addition salts with physiologically acceptable mineral or organic acids of the compound of formula (I) of claim 1.

7. The hydrochloride of the compound of formula (I) of claim 1.

8. The compound of formula (I) of claim 1.

9. The medicament according to claim 2, for the attack treatment of ulcerous gastro-duodenal disorders, wherein the compound of formula (I) or one of its salts is formed into oral unit doses between 200 and 400 mg.

10. The medicament according to claim 2, for the maintenance treatment of ulcerous gastro-duodenal disorders, wherein the compound of formula (I) or one of its salts is formed into oral unit doses between 100 and 200 mg.